(12) United States Patent
Buchholz et al.

(10) Patent No.: US 6,448,445 B1
(45) Date of Patent: Sep. 10, 2002

(54) METHOD FOR CATALYTICALLY DISUBSTITUTING CARBOXYLIC ACID AMIDES WITH AT LEAST ONE GRIGNARD REAGENT

(75) Inventors: Herwig Buchholz, Frankfurt; Urs Welz-biermann, Mannheim; Armin Meijere, Göttingen, all of (DE)

(73) Assignee: Merck Patent Gesellschaft mit beschraenkter Haftung (DE)

( * ) Notice: Subject to any disclaimer, the term of this patent is extended or adjusted under 35 U.S.C. 154(b) by 0 days.

(21) Appl. No.: 09/719,824
(22) PCT Filed: Jun. 18, 1999
(86) PCT No.: PCT/EP99/04252
§ 371 (c)(1), (2), (4) Date: Feb. 23, 2001
(87) PCT Pub. No.: WO99/65860
PCT Pub. Date: Dec. 23, 1999

(30) Foreign Application Priority Data

Jun. 18, 1998 (DE) .......................................... 198 27 166

(51) Int. Cl.[7] .............................................. C07C 209/66
(52) U.S. Cl. ........................ 564/414; 546/184; 564/446; 564/448; 564/452; 564/453; 564/455; 564/462; 564/471
(58) Field of Search ................................ 546/184, 446, 546/448, 452, 453, 455, 462, 471, 414; 564/446, 448, 452, 463, 455, 462, 471, 414

(56) References Cited

U.S. PATENT DOCUMENTS 4,020,059 A 4/1977 Isamu

FOREIGN PATENT DOCUMENTS

| DE | 2725245 | 12/1977 |
| DE | 2657476 | 6/1978 |
| GB | 807835 | 1/1959 |
| GB | 921943 | 3/1963 |

OTHER PUBLICATIONS

Kuffner F. et al.: "Ueber hochverzweigte aliphatische Verbindungen" Monatshefte FUeR Chemie, Bd. 93, 1962, Seiten 496–475, XP002117676 in der Anmeldung erwaehnt Manfred T. Reetz et al.: "Stereoselective addition of organotitanium reagents to carbonyl compounds" Chemische Berichte., Bd. 118, Nr. 4, 1985, Seiten 1441–1453, XP002117771 Verlag Chemie GmbH. Weinheim., DE ISSN: 0009–2940.

Manfred T. Reetz et al.: "Chemoselective addition of organotitanium reagents to carbonyl compounds" Chemische Berichte., Bd. 118, Nr. 4, 1985, Seiten 1421–1440, XP002117770 Verlag Chemie GmbH. Weinheim., DE ISSN: 0009–2940.

Vladimir Chaplinski et al.: "Eine nuetzliche Synthese von Cyclopropylaminen aus Carbonsaeurediakylamiden" Angewandte Chemie., Bd. 108, Nr. 4, 1996, Seiten 491–492, XP002117735 VCH Verlagsgesellschaft, Weinheim., DE ISSN: 0044–8249.

Yuying C. Hwang et al.: "A synthesis of &–substituted amines" Journal of Organic Chemistry., Bd. 50, Nr. 20, 1985, Seiten 3885–3890, XP002117673 Easton US.

Vladimir Chaplinski et al.: "A new versatile reagent for the synthesis of cyclopropylamines . . . " Synlett., 1997, Seiten 111–114, XP002117679 Thieme Verlag, Stuttgart., DE ISSN: 0936–5214.

"Houben–weyl, Methoden Der Organischen Chemie, vol. XI/1, S. 820–823" 1957, Georg Thieme Verlag, Stuttgart, DE XP002117680 Seite 820, Absatz 2 –Seite 823, Absatz 1.

Jerry March: "Adanced organic chemistry" 1985 John Wiley, New York. Chischester. Brisbane. Toronto. Singapore XP002117736 Seite 825, Abstaz 3.

"Beilsteins Handbuch Der Organischen Chemie, vierte Auflage, drittes und viertes Ergaenzungswerk, Bd 20, erster Teil, S. 316" 1977, Springer–Verlag, Berlin. Heidelberg. New York XP002117681 Seite 316, Absatz 3.

N. Maxim et al.: "Sur la methode de Bouveault...." Bulletin De La Societe Chimique De France., Bd. 5, Nr. 3, 1936, Seiten 1084–1093, XP002117677 Paris Fr.

*Primary Examiner*—Shailendra Kumar
(74) *Attorney, Agent, or Firm*—Millen, White, Zelano & Branigan, P.C.

(57) ABSTRACT

The invention relates to a method for disubstituting carboxylic acid amides on the geminal carbonyl-C-atom using at least one grignard reagent in the presence of a metal alcoholate compound used as a catalyst and in the presence of another organometallic compound used as a co-catalyst.

12 Claims, No Drawings

METHOD FOR CATALYTICALLY DISUBSTITUTING CARBOXYLIC ACID AMIDES WITH AT LEAST ONE GRIGNARD REAGENT

The present invention relates to processes for disubstituting carboxamides using at least one Grignard reagent in the presence of an organometallic compound as catalyst and a further organometallic compound as cocatalyst.

It is already known from the prior art that reactions of Grignard reagents with carbonyl compounds under catalytic action of tetraisopropyl orthotitanate results in cycloalkyl formation (O. G. Kulinovich, S. V. Sviridov, D. A. Vasilevskii, A. I. Savchenko, T. S. Pritytskaya, J. Org. Chem. USSR, 1991, 27, 250–253; O. G. Kulinovich, S. V. Sviridov, D. A. Vasilevskii, Synthesis, 1991, 234).

This course of the reaction with β-hydride elimination of the alkyl-substituted reagents is confirmed in the prior art below: (V. Chaplinski, Dissertation, Göttingen, 1996; V. Chaplinski, A. de Meijere, Angew. Chem. 1996, 108, 491; V. Chaplinski, H. Winsel, M. Kordes, A. de Meijere, Synlett, 1997, 111–114)

Accordingly, it was the object, in the reaction of carboxamides in the presence of organotitanium compounds, to suppress β-hydride elimination and thus cyclopropane formation, so that carboxamides can be converted, by disubstitution with Grignard reagents having two β-hydrogens among their substituents, into the corresponding substituted amino compounds.

According to the invention, this is achieved by using a catalyst system comprising an organometal compound as catalyst and a further organometal compound as cocatalyst.

Accordingly, the present invention provides a process for preparing compounds of the general formula (I)

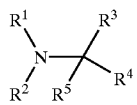

(I)

in which

R¹, R² and R³ independently of one another are H, A, Ar, —Si(R⁶)₃, —Sn(R⁶)₃, —SR⁷, —OR⁷, —NR⁸R⁹ or R¹ and R² or R¹ and R³ or R⁸ and R⁹ can be attached to one another and together form a cyclic ring having 3 to 8 C atoms which optionally contains, in addition to nitrogen, at least one further heteroatom selected from the group consisting of —S—, —O— and —NR⁶—, R⁴ and R⁵, which may be identical or different, are A, Ar, —Si(R⁶)₃, —Sn(R⁶)₃, —SR⁷, —OR⁷, —NR⁸R⁹, —C(R¹⁰) (R⁸)CH₂R⁹, in which R⁸, R⁹ and R¹⁰ or R⁴ and R⁵ are as defined above or R⁸ and R⁹ are attached to one another and together form a cyclic ring having 3 to 8 C atoms which optionally contains, in addition to one nitrogen atom, at least one heteroatom selected from the group consisting of —S—, —O—and —NR⁶—;

with the proviso that the radicals R⁴ and R⁵ in the β position in each case have at least two hydrogen atoms, R⁶, R⁷, R⁸ and R⁹ independently of one another are A or Ar, R¹⁰ is A, Ar, —Si(R⁶)₃, —Sn(R⁶)₃, —SR⁷, —OR⁷, —NR⁸R⁹, in which R⁸ and R⁹ are as defined above or R⁸ and R⁹ are attached to one another and together form a cyclic ring having 3 to 8 C atoms which optionally contains, in addition to one nitrogen atom, at least one heteroatom selected from the group consisting of —S—, —O— and —NR⁶—, A is a straight-chain or branched alkyl radical having from 1 to 10 C atoms, a straight-chain or branched alkenyl radical having 2 to 10 C atoms, or a straight-chain or branched alkynyl radical having 2–10 C atoms or a substituted or unsubstituted cycloalkyl radical having 3–8 C atoms, or a mono- or polyunsaturated cycloalkyl radical having 3–8 C atoms, and Ar is a substituted or unsubstituted aryl radical having 6–20 C atoms, characterized in that a compound of the general formula (II)

(II)

in which R¹, R² and R³ have the meanings given above for the formula (I) is reacted with in each case one nucleophilic reagent of the general formula (IIIa) and one nucleophilic reagent of the general formula (IIIb)

Z—R⁴ (IIIa)

Z—R⁵ (IIIb)

in which

R⁴ and R⁵ have the meaning given for the formula (I), and

Z is Li or MgX where x is Hal and

Hal is Cl, Br or I.

According to the invention, the process is carried out in the presence of catalytic amounts of a metal alkoxide of the general formula (VI):

MX₄₋ₙ(OR)ₙ (IV)

in which

M is titanium, zirconium or hafnium,

X is Cl, Br, I and

R is alkyl having 1 to 10 C atoms or aryl having 6 to 20 C atoms, n is an integer from 1 to 4.

Preference is given to using metal alkoxides in which R is isopropyl. Particular preference is given to using the metal alkoxide Ti(OiPr)₄ in which iPr is an isopropyl radical.

The present invention also provides a corresponding process which is carried out in the presence of a cocatalyst. Accordingly, the present invention includes a process which is carried out using metal isopropoxides and alkylsilyl halides as cocatalysts; i.e. metal isopropoxides of the general formula (V) and alkylsilyl halides of the general formula (VI)

M^(s+)(O-isopropyl)ₛ (V)

R₃SiX (VI)

or of the general formula (VII)

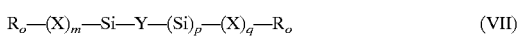

Rₐ—(X)ₘ—Si—Y—(Si)ₚ—(X)_q—Rₐ (VII)

in which
M' is Al, Ca, Na, K, Si or Mg, preferably Mg or Na,
s is an integer from 1 to 4 and is the oxidation state of the metal,
R is alkyl having 1 to 10 C atoms or aryl having 6 to 20 C atoms,
X is F, Cl, Br, CN,
m is 0, 1,
n is 1 to 10,
o is 0, 2, 3,
p is 0, 1
and
q is 0, 1,
with the proviso that o=3 and Y≈(CH$_2$)$_n$ if m=0.

Thus, the invention also provides a process, which is characterized in that
a) a carboxamide of the general formula (II), 1–15 mol %, based on the carboxamide, of a metal alkoxide selected from the group consisting of titanium alkoxide, zirconium alkoxide and hafnium alkoxide and, if appropriate, a cocatalyst are initially charged at room temperature under an atmosphere of inert gas in a solvent selected from the group consisting of toluene, THF, n-hexane, benzene and diethyl ether,
b) a solution comprising a nucleophilic reagent of the general formulae (IIIa) and (IIIb) is added dropwise and
c) the mixture is allowed to react with stirring and, after the reaction has ended, worked up in a customary manner.

Experiments have shown that, using a nucleophilic reagent of the general formula (IIIa) or (IIIb), which may be Grignard reagents and which may be added as such to the reaction mixture, it is possible to convert carboxamides of the general formula (II) in the presence of catalytic amounts of titanium alkoxide, zirconium alkoxide or hafnium alkoxide in a simple manner into symmetrically or unsymmetrically substituted compounds of the general formula (I).

According to the invention, using the process described herein, it is possible to convert, with good yields, carboxamides of the general formula (II) in which $R^1$, $R^2$ and $R^3$ independently of one another can have the following meanings:
H or
A i.e. branched or unbranched alkyl having 1–10 C atoms, such as methyl, ethyl, n- or isopropyl, n-, sec- or t-butyl, pentyl, hexyl, heptyl, octyl, nonyl, decyl and suitable isomers thereof, or cycloalkyl having 3–8 C atoms, such as cyclopropyl, cyclobutyl, -cyclopentyl, cyclohexyl, cycloheptyl, cyclooctyl, and corresponding methyl- or ethyl-substituted cycloalkyl groups, or mono- or polyunsaturated cycloalkyl groups, such as cyclopentenyl or cyclopentadienyl, or branched or unbranched alkenyl having 2 to 10 C atoms, such as allyl, vinyl, isopropenyl, propenyl, or branched or unbranched alkynyl having 2 to 10 C atoms, such as ethynyl, propynyl, or
aryl having 6 to 20 C atoms which is either unsubstituted or mono- or polysubstituted, such as phenyl, naphthyl, anthryl, phenanthryl, mono- or polysubstituted by substituents selected from the group consisting of NO$_2$, F, Cl, Br, NH$_2$, NHA, NA$_2$, OH and OA, where A can have the meanings given above, can be mono-, poly-, or fully halogenated, preferably fluorinated, or aralkenyl or aralkynyl, where the aryl, alkenyl and alkynyl groups can in each case have the given meanings, such as, for example, in phenylethynyl.

Good yields are in particular also obtained using carboxamides in which $R^1$ and $R^2$ or $R^1$ and $R^3$ together form a cyclic ring having 3–8 C atoms which, in addition to nitrogen, contains further heteroatoms, such as —S—, —O— or —NR$^6$—. Particular preference is given here to compounds in which $R^1$ and $R^2$ or $R^1$ and $R^3$ form a simple cyclic ring which includes the nitrogen of the carboxamide or in which $R^1$ and $R^2$ or $R^1$ and $R^3$ form a cyclic ring which contains, as further heteroatom, an oxygen atom.

Thus, high yields are obtained in this manner when the starting materials used are compounds such as, for example,

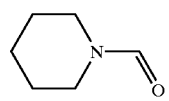

or

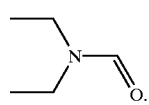

The nucleophilic reagent used can be a Grignard reagent or an organolithium compound of the general formulae (IIIa) or (IIIb), in which the radicals
$R^4$ and $R^5$ are preferably an alkyl radical having 1 to 10 C atoms, such as ethyl, n- or isopropyl, n- or sec-butyl, pentyl, hexyl, heptyl, octyl, nonyl, decyl and suitable isomers thereof, or cycloalkyl having 3–8 C atoms, such as cyclopropyl, cyclobutyl, cyclopentyl, cyclohexyl, cycloheptyl, cyclooctyl or corresponding methyl- or ethyl- substituted cycloalkyl groups or mono- or polyunsaturated cycloalkyl groups, such as cyclopentenyl or cyclopentadienyl, or branched or unbranched alkenyl having 2 to 10 C atoms, such as allyl, vinyl, isopropenyl, propenyl, or branched or unbranched alkynyl having 2 to 10 C atoms, such as propynyl,
$R^8$, $R^9$ and $R^{10}$ preferably represent an alkyl radical having 1 to 10 C atoms, such as methyl, ethyl, n- or isopropyl, n-, sec- or t-butyl, pentyl, hexyl, heptyl, octyl, nonyl, decyl and suitable isomers thereof, or cycloalkyl having 3–8 C atoms, such as cyclopropyl, cyclobutyl, cyclopentyl, cyclohexyl, cycloheptyl, cyclooctyl, or corresponding methyl- or ethyl- substituted cycloalkyl groups, or mono- or polyunsaturated cycloalkyl groups, such as cyclopentenyl or cyclopentadienyl, or branched or unbranched alkenyl having 2 to 10 C atoms, such as allyl, vinyl, isopropenyl, propenyl, or branched or unbranched alkynyl having 2 to 10 C atoms, such as ethynyl, propynyl,
or are aryl radicals having 6 to 20 C atoms which is either unsubstituted or mono- or polysubstituted, such as phenyl, napthyl, anthryl, phenanthryl, mono- or polysubstituted by substituents selected from the group consisting of NO$_2$, F, Cl, Br, NH$_2$, NHA, NA$_2$, OH and OA, where A can have the meanings given above, can be mono-, poly- or- fully halogenated, preferably fluorinated,
or are aralkyl radicals having 7 to 20 C atoms, such as benzyl, optionally mono- or polysubstituted by substituents selected from the group consisting of $NO_2$, F, Cl, Br, $NH_2$, NHA, $NA_2$, OH and OA, where A can have the meanings given above, can be mono-, poly- or fully halogenated, preferably fluorinated, or are aralkenyl or aralkynyl radicals, where the aryl, alkenyl and alkynyl group can in each case have the given meanings, such as, for example, in phenyl- ethynyl.

Furthermore, the radicals $R^4$ and $R^5$ in the general formulae (IIIa) and (IIIb) can be $-Si(R^6)_3$, $-Sn(R^6)_3$, $-SR^7$, $-OR^7$, $-NR^8R^9$, $-C(R^{10})R^8CH_2R^9$, in which $R^6$, $R^7$, $R^8$, $R^9$ and $R^{10}$ independently of one another have the above-mentioned meanings or $R^8$ and $R^9$ are attached to one another and together form a cyclic ring having 3 to 8 C atoms which may optionally, in addition to a nitrogen atom, contain at least one heteroatom selected from the group consisting of $-S-$, $-O-$ and $-NR^6-$.

The radical Z in the general formulae (IIIa) and (IIIb) preferably represents a radical MgX where X is Cl or Br, or the radical Z is lithium.

Particular preference according to the invention is given to using Grignard compounds such as: ethylmagnesium bromide, n- or isopropylmagnesium bromide, iso- or sec-butylmagnesium bromide, n- hexylmagnesium bromide, cyclohexylmagnesium chloride, vinylmagnesium bromide, cyclopentylmagnesium bromide, cyclopentylmagnesium chloride, or mixtures thereof, for the reaction.

Thus, the invention also provides the compounds of the general formula (I) in which the radicals $R^1$ to $R^5$ can have the meanings described.

Furthermore, it was found that only if a cocatalyst is added, the geminal symmetric or unsymmetric dialkylation reactions according to the invention start even at room temperature and result in the complete conversion of the starting materials in a relatively short reaction time.

Suitable cocatalysts for this reaction are metal isopropoxides and alkylsilyl halides. Particularly suitable are metal isopropoxides of the general formula (V) and alkylsilyl halides of the general formula (VI)

$$M'^{(s+)}(\text{O-isopropyl})_s \quad (V)$$

$$R_3SiX \quad (VI)$$

or of the general formula (VII)

$$R_o-(X)_m-Si-Y-(Si)_p-(X)_q-R_o \quad (VII)$$

in which

M' is Al, Ca, Na, K, Si or Mg, preferably Mg or Na, s is an integer from 1 to 4 and is the oxidation state of the metal, R is alkyl having 1 to 10 C atoms or aryl having 6 to 20 C atoms, X is F, Cl, Br, CN, m is 0, 1, n is 1 to 10, o is 0, 2, 3, p is 0, 1 and q is 0, 1, with the proviso that o=3 and $Y \approx (CH_2)_n$ if m=0.

Preference is given to using metal isopropoxides in which s is an integer from 1 to 4 and is the oxidation state of the metal and M' is Al, Ca, Na, K, Si or Mg. Particular preference is given to Mg or Na.

Preference is given to using alkylsilyl halides in which R is alkyl having 1 to 6 C atoms. Particular preference is given to those in which R is alkyl having 1 to 3 C atoms and X is chlorine.

Particularly suitable cocatalysts are, inter alia, the following silicon compounds:

$(CH_3)_3SiCl$ $(CH_3)_2ClSi(CH_2)_2SiCl(CH_3)_2$ $(CH_3)_2ClSi(CH_2)_3CN$ $[(CH_3)_3Si]_2O$ $[(CH_3)_3Si]_2NH$ and $[(CH_3)_3Si]_2$.

It has been found that the addition of from 0.7 to 1.2 mol, in particular from 0.9 and 1.1 mol, of a cocatalyst based on one mol of starting material leads to improved results, such as, for example, higher yields, lower reaction temperature or shorter reaction times.

As can be demonstrated using examples, under favourable conditions a complete conversion of the carboxamide according to the general equation (Eq. 1) has taken place after just one hour:

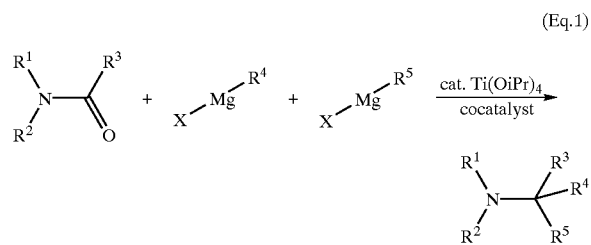

(Eq.1)

For carrying out the process according to the invention, the catalyst used can be a commercial metal alkoxide selected from the group consisting of titanium alkoxide, zirconium alkoxide and hafnium alkoxide. Preference is given to using titanium tetraisopropoxide. The metal alkoxide, preferably titanium tetraisopropoxide, is used as a solution in a suitable solvent, which is dried beforehand. Suitable solvents are, for example aliphatic or aromatic hydrocarbons or ethers. Preference is given to using solvents selected from the group consisting of toluene, THF, n-hexane, benzene and diethyl ether, which are dried prior to the reaction by methods known to the person skilled in the art. Drying can be carried out with the aid of magnesium sulphate, calcium chloride, sodium, potassium hydroxide or by other methods.

A preferred embodiment of the process according to the invention comprises initially charging the titanium tetraisopropoxide used as catalyst in an amount of from 1 to 15, preferably 1.5 to 14, in particular 2 to 10 and very particularly preferably from 3 to 6 mol %, based on one mol of the amide used as starting material, in the form of a solution adjusted to a temperature of from 10 to 30° C., preferably 15–25° C., particularly preferably to a temperature of about 20° C. Under an atmosphere of inert gas (nitrogen or argon), the starting material, either as such in liquid form or dissolved in a solvent selected from the group consisting of toluene, THF, n-hexane, benzene and diethyl ether, is slowly added dropwise with stirring. An amount of cocatalyst which corresponds to the amount to be reacted is then added dropwise, if required likewise in a solvent. The reaction mixture obtained is stirred for a short period, i.e. for a few minutes, at a constant temperature. Such an amount of the nucleophilic reagent of the general formulae (IIIa) and (IIIb), in particular Grignard reagent, is then slowly added to the resulting reaction mixture that substitution of the geminal carbonyl C atom by two identical or different substituents, i.e. a symmetric or unsymmetric substitution of the geminal carbonyl C atom, can take place. The addition of the nucleophilic reagents according to the invention prepared by methods generally known to the person skilled in the art should take place at such a rate that the temperature of the reaction mixture does not exceed 50° C. It is advantageous to carry out the addition of the nucleophilic reagents, i.e. of the Grignard reagents or the lithium compounds, with efficient mixing, preferably vigorous stirring. To shift the reaction equilibrium to the side of the desired symmetrically or unsymmetrically substituted product, the nucleophilic reagents used, preferably Grignard reagents, are in each case added in amounts of from 0.7 to 1.2 mol per mole of starting material that participates in the reaction. Preference is given to adding the Grignard reagents in amounts of from 0.9 to 1.1 mol, based on 1 mol of starting material.

After the addition of the Grignard reagents has ended, the reaction mixture is stirred for some time at a constant temperature, until the reaction is brought to completion.

Thus, by the synthesis according to the invention it is possible to prepare symmetrically and unsymmetrically substituted amino compounds of the general formula (I) with good or satisfactory yields within adequate reaction times. In an advantageous manner, it is possible, by adding one of the catalysts in combination with one of the cocatalyst compounds described of the general formulae (V), (VI) or (VII), to reduce the reaction times considerably, in the most favourable case to one hour, without this. resulting in a reduction in the yields obtained.

Thus, the present invention also provides the use of a catalyst system comprising a metal alkoxide selected from the group consisting of titanium alkoxide, zirconium alkoxide and hafnium alkoxide as catalyst and a compound of the general formulae (V), (VI) or (VII) with the meanings given above, and the use of this catalyst system for preparing the unsymmetrically substituted compounds of the general formula (I).

For example, 5 mmol of starting material are, at 20° C. and under an atmosphere of inert gas, added dropwise with stirring to a solution of 3 mol % of titanium tetraisopropoxide in 40 ml of dried tetrahydrofuran. 5 mmol of cocatalyst, likewise taken up in dried tetrahydrofuran, are added slowly with stirring to this mixture. The mixture is stirred at 20° C. for 5 minutes, and a solution of in each case 6 mmol of two different Grignard reagents is then added at such a rate that the temperature of the reaction mixture does not exceed 50° C. Stirring is continued for one hour, until the reaction has gone to completion.

After the reaction according to the invention, work-up of the reaction mixture can be carried out in a manner known to the person skilled in the art.

Here, the products can be precipitated as salts using solutions of hydrochloric acid, for example a 1 molar ethereal solution of hydrochloric acid, and be filtered off and, if required, purified by recrystallization.

To remove the Lewis acid, it is possible, for example, to add a suitable amount of saturated ammonium chloride solution and water, followed by further vigorous stirring for a plurality of hours (1–3 hours) . The resulting precipitate is separated off and washed with a little ether, preferably diethyl ether. The filtrate is made alkaline (pH>10) by addition of a suitable base, such as an NaOH, KOH, sodium carbonate or potassium carbonate solution, preferably sodium hydroxide solution. The phases that are formed are then separated, and the aqueous phase is extracted repeatedly (for example in the special case given above three times with in each case 30 ml) with diethyl ether. The combined organic phases are washed with (for example 15 ml of) saturated sodium chloride solution and can be dried over potassium carbonate, magnesium sulphate or sodium sulphate and filtered.

The products can be purified by various routes using methods known to the person skilled in the art, such as, for example, in the following manner:

1. They are precipitated as hydrochlorides using 1 M ethereal hydrochloric acid solution and filtered off (the resulting product is, if required, purified by recrystallization).
2. The organic phase is extracted repeatedly with a 0.5 M acid solution, preferably an aqueous hydrochloric acid solution. The extract obtained is adjusted to pH>10 using bases, preferably 2 M aqueous sodium hydroxide solution, and extracted at least once, preferably repeatedly, with diethyl ether. The resulting organic phases, which contain the reaction product, can be dried, if appropriate, over potassium carbonate, magnesium sulphate or sodium sulphate and be freed from the organic solvent under reduced pressure.
3. Furthermore, it is possible to isolate the reaction product by removing the organic solvent under reduced pressure and separating the residue that remains by column chromatography, to isolate the reaction product.

In the general description of the process procedure given above, the Grignard reagents can also be replaced by the corresponding lithium compounds. The corresponding lithium compounds, like the Grignard reagents, can be prepared by methods generally known to the person skilled in the art, and they can be reacted according to the invention in the same manner as described above.

The compounds of the general formula (I) prepared according to the invention can be used, for example, as intermediates in the preparation of sulphur- or selenium-containing amines for the chiral catalysis of diethyl zinc syntheses (literature: Werth, Thomas; Tetrahydron Lett. 36; 1995, 7849–7852, Werth, Thomas et al. Helv. Chim. Acta 79, 1996, 1957–1966).

To illustrate and better understand the present invention, examples are given below. However, owing to the general validity of the described principle of the invention, they are not meant to reduce the scope of the present application to just these examples.

EXAMPLES

Titanium-tetraisopropoxide-induced symmetric and unsymmetric dialkylation of carboxamides using at least one Grignard reagent.

According to the reaction shown in Equation 1, the following reactions were carried out using one equivalent of $(CH_3)_3SiCl$ as cocatalyst:

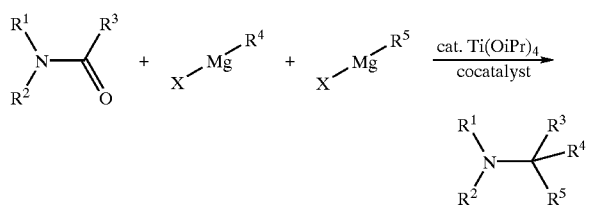

(Eq.1)

Examples 1 to 6

At 20° C. and under an atmosphere of nitrogen, 5 mmol of the amide listed in Table 1 and 5 mmol of $(CH_3)_3SiCl$ as cocatalyst are added dropwise to a solution of 3 mol % of $Ti(OiPr)_4$, based on the amide given in Table 1, in 40ml of dry tetrahydrofuran. The mixture is stirred at 20° C. for 5 min. 12 mmol or in each case 6 mmol of the Grignard reagents given in Table 1 are then added to the reaction mixture at such a rate that the temperature of the reaction mixture does not exceed 50° C. The mixture is then stirred at the reaction temperature given in Table 1 for the reaction time given in Table 1, until the reaction has, ended.

Work-up of the reaction products:

To remove the Lewis acid, 15 ml of saturated ammonium chloride solution and 15 ml of water are added with vigorous stirring (1 hour).

Any precipitate that is formed is filtered off with suction using a nutsch/suction flask, and the filter residue is washed with twice 20 ml of dry diethyl ether. The filtrate is made alkaline (pH≧10) by addition of sodium hydroxide solution.

The phases are then separated in a separating funnel. The aqueous phase is extracted three times with in each case 30 ml of diethyl ether. The combined organic phases are washed with saturated sodium chloride solution and the separated organic phase is dried over potassium carbonate and filtered. The solvent is removed using a rotary evaporator. The residue is chromatographed over 20 g of silica gel, using a mixture of heptane/tert-butyl methyl ether 50/1 as mobile phase.

TABLE 1

$Ti(OiPr)_4$-induced reaction of carboximides with $R^4MgX$ and $R^5MgX$

| Amide | Product | Yield | $R^4CH_2CH_2$—MgX | Reaction conditions |
|---|---|---|---|---|
| | | 48% | n-Hexyl-MgBr/ EtMgBr | 1 h/RT/3 mol % $Ti(OiPr)_4$/I equiv. cocat |
| | | 50% | VinylMgBr | 1 h/RT/3 mol % $Ti(OiPr)_4$/I equiv. cocat |
| | | 89% | EtMgBr | 1 h/RT/3 mol % $Ti(OiPr)_4$/I equiv. cocat |
| | | 50% | Cyclo-pentyl-MgBr | 1 h/RT/3 mol % $Ti(OiPr)_4$/I equiv. cocat |
| | | 60% | Cyclohexyl-MgCl | 1 h/RT/3 mol % $Ti(OiPr)_4$/I equiv. cocat |

What is claimed is:

1. A process for preparing compounds of formula (I)

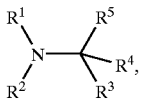 (I)

in which

R$^1$, R$^2$ and R$^3$ independently of one another are H, A, Ar, —Si(R$^6$)$_3$, —Sn(R$^6$)$_3$, —SR$^7$, —OR$^7$, —NR$^8$R$^9$ or R$^1$ and R$^2$ or R$^1$ and R$^3$ or R$^8$ and R$^9$ can be attached to one another and together form a cyclic ring having 3 to 8 C atoms which optionally contains, in addition to nitrogen, at least on further heteroatom selected from the group consisting of —S—, —O— and —NR$^6$—, R$^4$ and R$^5$, which may be identical or different, are A, Ar, —Si(R$^6$)$_3$, —SN(R$^6$)$_3$, —SR$^7$, —OR$^7$, —NR$^8$R$^9$, —C(R$^{10}$)(R$^8$)CH$_2$R$^9$, in which R$^8$, R$^9$ and R$^{10}$ are as defined above or R$^8$ and R$^9$ are attached to one another and together form a cyclic ring having 3 to 8 C atoms which optionally contains, in addition to one nitrogen atom, at least one heteroatom selected from the group consisting of —S—, —O— ad —NR$^6$—; with the proviso that the radicals R$^4$ and R$^5$ in the β position in each case have at least two hydrogen atoms, R$^6$, R$^7$, R$^8$ and R$^9$ independently of one another are A or Ar, R$^{10}$ is A, Ar, —Si(R$^6$)$_3$, —SN(R$^6$)$_3$, —SR$^7$, —OR$^7$, —NR$^8$R$^9$, in which R$^8$ and R$^9$ are as defined above or R$^8$ and R$^9$ are attached to one another and together form a cyclic ring having 3 to 8 C atoms which optionally contains, in addition to one nitrogen atom, at least one heteroatom selected from the group consisting of —S—, —O— and NR$^6$—, A is a straight-chain or branched alkyl radical having from 1 to 10 C atoms, a straight-chain or branched alkenyl radical having 2 to 10 C atoms, or a straight-chain or branched alkynyl radical having 2–10 C atoms or a substituted or unsubstituted cycloalkyl radical having 3–8 C atoms, or a mono- or polyunsaturated cycloalkyl radical having 3–8 C atoms, and Ar is a substituted or unsubstituted aryl radical having 6–20 C atoms, comprising reacting a compound of formula (II)

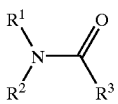 (II)

in which R$^1$, R$^2$ and R$^3$ have the meanings given above for the formula (I) is reacted with in each case one nucleophilic reagent of the general formula (IIIa) and one nucleophilic reagent of formula (IIIb)

 (IIIa)

 (IIIb)

in which

R$^4$ and R$^5$ have the meaning given for the formula (I), and

Z is Li or MgX where x is Hal and

Hal is Cl, Br or I, wherein the process is carried out in the presence of catalytic amounts of a metal alkoxide selected from the group consisting of titanium alkoxide, zirconium alkoxide and hafnium alkoxide, and wherein the process is carried out in the presence of a cocatalyst.

2. Process according to claim 1, characterized in that it is carried out in the presence of a metal isopropoxide or an alkylsilyl halide cocatalyst.

3. Process according to claim 1, wherein the cocatalyst used is a metal isopropoxide of the general formula (V) or an alkylsilyl halide of the general formula (VI)

 (V)

 (VI)

or of the general formula (VII)

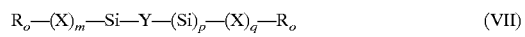 (VII)

in which

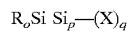

M' is Al, Ca, Na, K Si or Mg, preferably Mg or Na, s is an integer from 1 to 4 and is the oxidation state of the metal, R is alkyl having 1 to 10 C atoms or aryl having 6 to 20 atoms, X is F, Cl, Br, CN, m is 0, 1, n is 1 to 10, o is 0, 2, 3, p is 0, 1 q is 0, 1, and y is an alkyl group of CH$_2$ or greater, with the proviso that o=3 and Y≠(CH$_2$)$_n$ if M=0.

4. Process according to claim 1, wherein the catalyst used is a metal alkoxide of the general formula (IV)

 (IV)

in which

M is titanium, zirconium or hafnium,

X is Cl, Br, I and

R is alkyl having 1 to 10 C atoms or aryl having 6 to 20 C atoms, n is an integer from 1 to 4.

5. A process according to claim 1, further comprising:

a) initially charging a carboxamide of the general formula (II), 1–15 mol %, based on the carboxamide, of the metal alkoxide selected from the group consisting of titanium alkoxide, zirconium alkoxide and hafnium alkoxide and, optionally, the cocatalyst at 10–30° C. under an atmosphere of inert gas in a solvent selected from the group consisting of toluene, THF, n-hexane, benzene and diethyl ether, b) adding dropwise a solution comprising two identical or different nucleophilic reagents of the general formulae (IIIa) and (IIIb)

in which

R$^4$ and R$^5$ have the meanings given in claim 1 and c) reacting the mixture with stirring.

6. Process according to claim 5, wherein a) is carried out at a temperature of from 15 to 25° C.

13

7. Process according to claim 5, wherein a) is carried out at room temperature.

8. Process according to claim 1, wherein the nucleophilic reagents used are lithium compounds of the general formulae (IIIa) and (IIIb).

9. Process according to claim 1, wherein nucleophilic reagents used are compounds of the general formulae (IIIa) and (IIIb) in which $R^4$ and $R^5$ are ethyl, n- or isopropyl, iso- or sec-butyl, n-hexyl, cyclopentyl, cyclohexyl, vinyl.

10. Process according to claim 1, wherein the compound that is reacted is a compound of the general formula (II) in which $R^1$, $R^2$ and $R^3$ independently of one another are H, methyl, ethyl, n- or isopropyl, iso-, sec- or tert-butyl, n-hexyl, phenyl or benzyl.

11. A process for preparing compounds of formula (I)

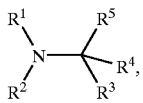
(I)

in which

R$^1$, R$^2$ and R$^3$ independently of one another are H, A, Ar, —Si(R$^6$)$_3$, —Sn(R$^6$)$_3$, —SR$^7$, —OR$^7$, —NR$^8$R$^9$ or R$^1$ and R$^2$ or R$^1$ and R$^3$ or R$^8$ and R$^9$ can be attached to one another and together form a cyclic ring having 3 to 8 C atoms which optionally contains, in addition to nitrogen, at least on further heteroatom selected from the group consisting of —S—, —O— and —NR$^6$—, R$^4$ and R$^5$, which may be identical or different, are A, Ar, —Si(R$^6$)$_3$, —SN(R$^6$)$_3$, —SR$^7$, —OR$^7$, —NR$^8$R$^9$, —C(R$^{10}$)(R$^8$)CH$_2$R$^9$, in which R$^8$, R$^9$ and R$^{10}$ are as defined above or R$^8$ and R$^9$ are attached to one another and together form a cyclic ring having 3 to 8 C atoms which optionally contains, in addition to one nitrogen atom, at least one heteroatom selected from the group consisting of —S—, —O— ad —NR$^6$—; with the proviso that the radicals R$^4$ and R$^5$ in the β position in each case have at least two hydrogen atoms, R$^6$, R$^7$, R$^8$ and R$^9$ independently of one another are A or Ar, R$^{10}$ is A, Ar, —Si(R$^6$)$_3$, —SN(R$^6$)$_3$, —SR$^7$, —OR$^7$, —NR$^8$R$^9$, in which R$^8$ and R$^9$ are as defined above or R$^8$ and R$^9$ are attached to one another and together form a cyclic ring having 3 to 8 C atoms which optionally contains, in addition to one nitrogen atom, at least one heteroatom selected from the group consisting of —S—, —O— and NR$^6$—, A is a straight-chain or branched alkyl radical having from 1 to 10 C atoms, a straight-chain or branched alkenyl radical having 2 to 10 C atoms, or a straight-chain or branched alkynyl radical having 2–10 C atoms or a substituted or unsubstituted cycloalkyl radical having 3–8 C atoms, or a mono- or polyunsaturated cycloalkyl radical having 3–8 C atoms, and Ar is a substituted or unsubstituted aryl radical having 6–20 C atoms, comprising reacting a compound of formula (II)

14

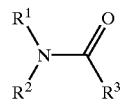
(II)

in which R$^1$, R$^2$ and R$^3$ have the meanings given above for the formula (I) is reacted with in each case one nucleophilic reagent of the general formula (IIIa) and one nucleophilic reagent of formula (IIIb)

Z—R$^4$ (IIIa)

Z—R$^5$ (IIIb)

in which

R$^4$ and R$^5$ have the meaning given for the formula (I), and

Z is Li or MgX where x is Hal and

Hal is Cl, Br or I, wherein the process is carried out in the presence of catalytic amounts of a metal alkoxide selected from the group consisting of titanium alkoxide, zirconium alkoxide and hafnium alkoxide.

12. A process for preparing compounds of formula (I)

(I)

in which

R$^1$, R$^2$ and R$^3$ independently of on another are H, A, Ar, —Si(R$^6$)$_3$, —Sn(R$^6$)$_3$, —SR$^7$, —OR$^7$, —NR$^8$R$^9$ or R$^1$ and R$^2$ or R$^1$ and R$^3$ or R$^8$ and R$^9$ can be attached to one another and together form a cyclic ring having 3 to 8 C atoms which optionally contains, in addition to nitrogen, at least on further heteroatom selected from the group consisting of —S—, —O— and —NR$^6$—, R$^4$ and R$^5$, which are different from each other, are A, Ar, —Si(R$^6$)$_3$, —SN(R$^6$)$_3$, —SR$^7$, —OR$^7$, —NR$^8$R$^9$, —C(R$^{10}$)(R$^8$)CH$_2$R$^9$, in which R$^8$, R$^9$ and R$^{10}$ are as defined above or R$^8$ and R$^9$ are attached to one another and together form a cyclic ring having 3 to 8 C atoms which optionally contains, in addition to one nitrogen atom, at least one heteroatom selected from the group consisting of —S—, —O— ad —NR$^6$—; with the proviso that the radicals R$^4$ and R$^5$ in the β position in each case have at least two hydrogen atoms, R$^6$, R$^7$, R$^8$ and R$^9$ independently of one another are A or Ar, R$^{10}$ is A, Ar, —Si(R$^6$)$_3$, —SN(R$^6$)$_3$, —SR$^7$, —OR$^7$, —NR$^8$R$^9$, in which R$^8$ and R$^9$ are as defined above or R$^8$ and R$^9$ are attached to one another and together form a cyclic ring having 3 to 8 C atoms which optionally contains, in addition to one nitrogen atom, at least one heteroatom selected from the group consisting of —S—, —O— and NR$^6$—, A is a straight-chain or branched alkyl radical having from 1 to 10 C atoms, a straight-chain or branched alkenyl radical having 2 to 10 C atoms, or a straight-chain or branched alkynyl radical having 2–10 C atoms or a substituted or unsubstituted cycloalkyl radical having 3–8 C atoms, or a mono- or polyunsaturated cycloalkyl radical having 3–8 C atoms, and Ar is a substituted or unsubstituted aryl radical having 6–20 C atoms, comprising reacting a compound of formula (II)

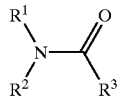
(II)

in which $R^1$, $R^2$ and $R^3$ have the meanings given above for the formula (I) is reacted with in each case one nucleophilic reagent of the general formula (IIIa) and one nucleophilic reagent of formula (IIIb)

$$Z-R^4 \quad \text{(IIIa)}$$

$$Z-R^5 \quad \text{(IIIb)}$$

in which $R^4$ and $R^5$ have the meaning given for the formula (I), and

Z is Li or MgX where

X is Hal and

Hal is Cl, Br or I, wherein the process is carried out in the presence of catalytic amounts of a metal alkoxide selected from the group consisting of titanium alkoxide, zirconium alkoxide and hafnium alkoxide.

* * * * *